United States Patent
Matsuda

(10) Patent No.: US 9,358,217 B2
(45) Date of Patent: *Jun. 7, 2016

(54) METHODS FOR REDUCING TRIGLYCERIDE, TOTAL CHOLESTEROL AND LOW DENSITY LIPOPROTEIN BLOOD LEVELS

(71) Applicant: MediciNova, Inc., La Jolla, CA (US)

(72) Inventor: Kazuko Matsuda, Beverly Hills, CA (US)

(73) Assignee: MediciNova, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/540,766

(22) Filed: Nov. 13, 2014

(65) Prior Publication Data

US 2015/0080471 A1 Mar. 19, 2015

Related U.S. Application Data

(63) Continuation of application No. 14/339,331, filed on Jul. 23, 2014.

(60) Provisional application No. 61/858,450, filed on Jul. 25, 2013.

(51) Int. Cl.
*A01N 37/10* (2006.01)
*A61K 31/19* (2006.01)
*A61K 31/192* (2006.01)

(52) U.S. Cl.
CPC .................................. *A61K 31/192* (2013.01)

(58) Field of Classification Search
USPC ........................................................ 514/571
See application file for complete search history.

(56) References Cited

U.S. PATENT DOCUMENTS

| | | |
|---|---|---|
| 4,788,055 A | 11/1988 | Fischer et al. |
| 4,816,264 A | 3/1989 | Phillips et al. |
| 4,828,836 A | 5/1989 | Elger et al. |
| 4,834,965 A | 5/1989 | Martani et al. |
| 4,834,985 A | 5/1989 | Elger et al. |
| 4,985,585 A | 1/1991 | Ohashi et al. |
| 4,996,047 A | 2/1991 | Kelleher et al. |
| 5,071,646 A | 12/1991 | Malkowska et al. |
| 5,133,974 A | 7/1992 | Paradissis et al. |
| 5,290,812 A | 3/1994 | Ohashi et al. |
| 7,060,854 B2 | 6/2006 | Locke et al. |
| 7,064,146 B2 | 6/2006 | Locke et al. |
| 2005/0239902 A1 | 10/2005 | Locke et al. |

FOREIGN PATENT DOCUMENTS

| | | |
|---|---|---|
| EP | 1 894 576 A1 | 3/2008 |
| WO | WO 2006/004803 A1 | 1/2006 |

OTHER PUBLICATIONS

Liu et al. ( "Cilostazol (Pietal®): a dual inhibitor of cyclic nucleotide phosphodiesterase type 3 and adenosine uptake." Cardiovascular drug reviews 19.4 (2001): 369-386).*
International Search Report and Written Opinion of the International Searching Authority issued in corresponding International Application No. PCT/US2014/047797 dated Oct. 24, 2014.

* cited by examiner

*Primary Examiner* — Layla Soroush
(74) *Attorney, Agent, or Firm* — Gilberto M. Villacorta; Lydia B. Choi; Foley & Lardner LLP

(57) ABSTRACT

A compound of Formula (I):

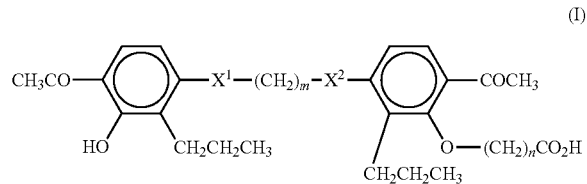

or a metabolite thereof, or an ester of the compound of Formula (I) or the metabolite thereof, or a pharmaceutically acceptable salt of each thereof, wherein m, n, $X^1$ and $X^2$ are as defined herein, is useful for reducing blood levels of one or more of triglycerides (TG), total cholesterol (TC) and low density lipoprotein (LDL) in human subjects.

29 Claims, No Drawings

METHODS FOR REDUCING TRIGLYCERIDE, TOTAL CHOLESTEROL AND LOW DENSITY LIPOPROTEIN BLOOD LEVELS

CROSS REFERENCE TO RELATED APPLICATIONS

This application claims priority to U.S. application Ser. No. 14/339,331 filed Jul. 23, 2014, which claims priority to U.S. Provisional Application No. 61/858,450 filed Jul. 25, 2013, the content of each which is incorporated herein in its entirety by reference.

FIELD OF THE INVENTION

This invention relates to reducing elevated levels of triglycerides, total cholesterol, and/or low density lipoproteins in patients by administering phenoxyalkylcarboxylic acids such as MN-001 and MN-002.

BACKGROUND OF THE INVENTION

Hyperlipidemia or hyperlipoproteinemia involves abnormally elevated levels of any or all lipids and/or lipoproteins in the blood and are risk factors for diseases such as cardiovascular diseases, due to, for example, their influence on atherosclerosis.

SUMMARY OF THE INVENTION

In one aspect, provided herein is a method of reducing a triglyceride blood level in a subject, comprising administering to a subject in need thereof an effective amount of a compound of Formula (I):

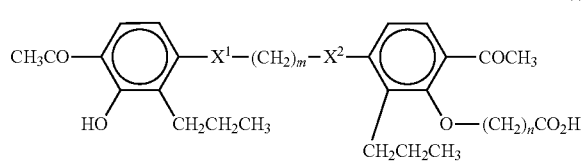

a metabolite thereof, an ester of the compound of Formula (I) or the metabolite thereof, or a pharmaceutically acceptable salt of each of the foregoing, in which m is an integer from 2 to 5, n is an integer from 3 to 8, $X^1$ and $X^2$ each independently represent a sulfur atom, oxygen atom, sulfinyl group, or a sulfonyl group, provided that $X^1$ and $X^2$ cannot both be oxygen atoms.

In one embodiment, the subject is diagnosed with hypertriglyceridemia. In another embodiment, the subject has a triglyceride blood level that is considered normal.

In another aspect, provided herein is a method of reducing a total cholesterol blood level in a subject, comprising administering to a subject in need thereof an effective amount of a compound of Formula (I), or a metabolite thereof, or an ester of the compound of Formula (I) or the metabolite thereof, or a pharmaceutically acceptable salt of each thereof, wherein the compound of Formula (I) is defined as above.

In one embodiment, the subject is diagnosed with hypercholesterolemia. In another embodiment, the subject has a total cholesterol blood level that is considered normal.

In another aspect, provided herein is a method of reducing a low density lipoprotein (LDL) blood level in a subject, comprising administering to a subject in need thereof an effective amount of a compound of Formula (I), or a metabolite thereof, or an ester of the compound of Formula (I) or the metabolite thereof, or a pharmaceutically acceptable salt of each thereof, wherein the compound of Formula (I) is defined as above.

In one embodiment, the subject is diagnosed with hyperlipoproteinemia. In another embodiment, the subject has a low density lipoprotein blood level that is considered normal.

In a preferred embodiment, the compound of Formula (I) is a compound of Formula (IA) (or MN-001):

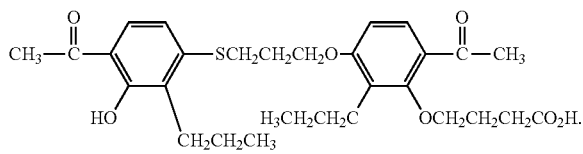

In another preferred embodiment, the metabolite of the compound of Formula (I) and (IA) is a compound of Formula (IB) (or MN-002):

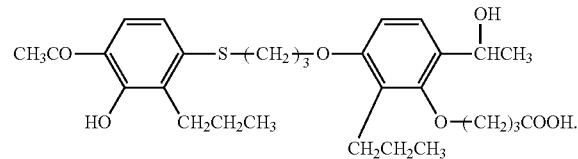

As an active metabolite of MN-001, the administration of effective amounts of MN-002 is expected to provide results similar to those observed for MN-001 administration.

It has been discovered that the administration of the compounds of the present invention to a subject results in a reduction in the blood levels of triglyceride (TG), total cholesterol (TC) and low density lipoprotein (LDL) compared to a control subject. Results from a variety of treatment subjects were studied, which showed the reduction in one or more of the foregoing substances after administration of a variety of dosage amounts of test drug under various treatment regimens, described in this disclosure. The treatment subjects included subjects suffering from a certain medical ailment, specifically, asthma or interstitial cystitis, but also included healthy subjects. No matter—the results showed that the blood chemistries of these treatment subjects were altered in a way that demonstrates the utility of the present invention in reducing TG, TC and LDL blood levels compared to control subjects, who received placebo. The present invention, therefore, is useful in the treatment of certain medical conditions, which are characterized by undesirable (usually elevated) blood levels of TG, TC and LDL. Such medical conditions include but are not limited to hypertriglyceridemia, hypercholesterolemia, or hyperlipoproteinemia. While the treatment regimens of individual subjects may vary according to a determination made by a knowledgeable medical practitioner or attending physician, in certain embodiments, it may be desirable to exclude from treatment a treatment subject who has been diagnosed with asthma or interstitial cystitis. In still other embodiments, it may also be desirable to exclude from treatment a treatment subject who has been diagnosed with non-alcoholic fatty liver disease or non-alcoholic steatohepatitis.

DETAILED DESCRIPTION OF THE INVENTION

Definitions

As used herein, and in the appended claims, the singular forms "a," "an" and "the" include plural references unless the context clearly dictates otherwise.

"Administering" or "Administration of" a drug to a patient (and grammatical equivalents of this phrase) includes both direct administration, including self-administration, and indirect administration, including the act of prescribing a drug. For example, as used herein, a physician who instructs a patient to self-administer a drug and/or provides a patient with a prescription for a drug is administering the drug to the patient.

"$C_x$" when placed before a group refers to the number of carbon atoms in that group to be X.

"Alkyl" refers to a monovalent acyclic hydrocarbyl radical having 1-12 carbon atoms. Non limiting examples of alkyl include methyl, ethyl, propyl, isopropyl, butyl, isobutyl, tertiary butyl, pentyl, hexyl and the like.

"Aryl" refers to a monovalent aromatic hydrocarbyl radical having up to 10 carbon atoms. Non-limiting examples of aryl include phenyl and naphthyl.

"Heteroaryl" refers to an aromatic group of from 1 to 10 carbon atoms and 1 to 4 heteroatoms selected from the group consisting of oxygen, nitrogen, sulfur within the aromatic ring, wherein the nitrogen and/or sulfur atom(s) of the heteroaryl are optionally oxidized (e.g., N-oxide, —S(O)— or —S(O)$_2$—). Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Non limiting examples of heteroaryl include pyridyl, pyrrolyl, indolyl, thiophenyl, and furyl.

"Cycloalkyl" refers to a monovalent non-aromatic cyclic hydrocarbyl radical having 3-12 carbon atoms. Non limiting examples of cycloalkyl include cyclopropyl, cyclobutyl, cyclopentyl, cyclohexyl, and the like.

"Heterocyclyl" refers to a monovalent non-aromatic cyclic group of 1 to 10 carbon atoms and 1 to 4 heteroatoms selected from the group consisting of oxygen, nitrogen, sulfur within the cycle, wherein the nitrogen and/or sulfur atom(s) of the heteroaryl are optionally oxidized (e.g., N-oxide, —S(O)— or —S(O)$_2$—). Such heteroaryl groups can have a single ring (e.g., piperidinyl or tetrahydrofuranyl) or multiple condensed rings wherein the condensed rings may or may not be aromatic and/or contain a heteroatom provided that the point of attachment is through an atom of the non-aromatic heterocyclyl group. Non limiting examples of heterocyclyl include pyrrolidinyl, piperidinyl, piperazinyl, and the like.

"Amino" refers to —NH$_2$.

"Alkylamino" refers to —NHR$_B$, wherein R$_B$ is C$_1$-C$_6$ alkyl optionally substituted with 1-3 aryl, heteroaryl, cycloalkyl, or heterocyclyl group.

"Dialkylamino" refers to —N(R$_B$)$_2$, wherein R$_B$ is defined as above.

"Comprising" shall mean that the methods and compositions include the recited elements, but not exclude others. "Consisting essentially of" when used to define methods and compositions, shall mean excluding other elements of any essential significance to the combination for the stated purpose. "Consisting of" shall mean excluding more than trace elements of other ingredients and substantial method steps for administering the compositions of this invention or process steps to produce a composition or achieve an intended result. Embodiments defined by each of these transitional terms and phrases are within the scope of this invention.

"Effective amount" of a compound utilized herein is an amount that, when administered to a patient with elevated levels of one or more of triglycerides, cholesterol, and LDL, will have the intended therapeutic effect, e.g., alleviation, amelioration, palliation or elimination of one or more manifestations of the medical condition in the patient. The full therapeutic effect does not necessarily occur by administration of one dose (or dosage), and may occur only after administration of a series of doses. Thus, an effective amount may be administered in one or more administrations.

"Pharmaceutically acceptable" refers to non-toxic and suitable for administration to a patient, including a human patient.

"Pharmaceutically acceptable salts" refer to salts that are non-toxic and are suitable for administration to patients. Non-limiting examples include alkali metal, alkaline earth metal, and various primary, secondary, and tertiary ammonium salts. When the ester of the compound of Formula (I) includes a cationic portion, for example, when the ester includes an amino acid ester, the salts thereof can include various carboxylic acid, sulfonic acid, and miner acid salts. Certain non-limiting examples of salts include sodium, potassium, and calcium salts.

"Protecting groups" refer to well-known functional groups which, when bound to a functional group, render the resulting protected functional group inert to the reaction to be conducted on other portions of a compound and the corresponding reaction condition, and which can be reacted to regenerate the original functionality under deprotection conditions. The protecting group is selected to be compatible with the remainder of the molecule. A "carboxylic acid protecting group" protects the carboxylic functionality of the phenoxyalkylcarboxylic acids during their synthesis. Non limiting examples of carboxylic acid protecting groups include, benzyl, p-methoxybenzyl, p-nitrobenzyl, allyl, benzhydryl, and trityl. Additional examples of carboxylic acid protecting groups are found in standard reference works such as Greene and Wuts, Protective Groups in Organic Synthesis., 2d Ed., 1991, John Wiley & Sons, and McOmie Protective Groups in Organic Chemistry, 1975, Plenum Press. Methods for protecting and deprotecting the carboxylic acids disclosed herein can be found in the art, and specifically in Greene and Wuts, supra, and the references cited therein.

"Treating" a medical condition or a patient refers to taking steps to obtain beneficial or desired results, including clinical results. For purposes of the various aspects and embodiments of the present invention, beneficial or desired clinical results include, but are not limited to, reduction, alleviation, or amelioration of one or more manifestations of or negative effects of, or associated with, elevated levels of one or more of triglycerides, cholesterol, and LDL, improvement in one or more clinical outcomes, diminishment of extent of disease, delay or slowing of disease progression, amelioration, palliation, or stabilization of the disease state, and other beneficial results described herein.

Preferred Embodiments

In one aspect, provided herein is a method of reducing a triglyceride blood level in a subject, comprising administering to a subject in need thereof an effective amount of a compound of Formula (I):

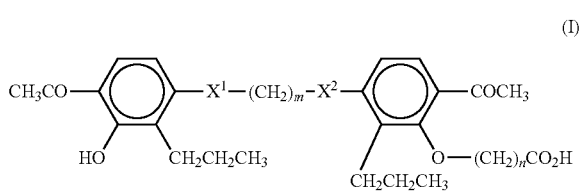

a metabolite thereof, an ester of the compound of Formula (I) or the metabolite thereof, or a pharmaceutically acceptable salt of each of the foregoing, in which m is an integer from 2 to 5, n is an integer from 3 to 8, $X^1$ and $X^2$ each independently represent a sulfur atom, oxygen atom, sulfinyl group, or a sulfonyl group, provided that $X^1$ and $X^2$ cannot both be oxygen atoms.

In one embodiment, the subject is diagnosed with hypertriglyceridemia. In another embodiment, the subject has a triglyceride blood level that is considered normal.

In another aspect, provided herein is a method of reducing a total cholesterol blood level in a subject, comprising administering to a subject in need thereof an effective amount of a compound of Formula (I), or a metabolite thereof, or an ester of the compound of Formula (I) or the metabolite thereof, or a pharmaceutically acceptable salt of each thereof, wherein the compound of Formula (I) is defined as above.

In one embodiment, the subject is diagnosed with hypercholesterolemia. In another embodiment, the subject has a total cholesterol blood level that is considered normal.

In another aspect, provided herein is a method of reducing a low density lipoprotein (LDL) blood level in a subject, comprising administering to a subject in need thereof an effective amount of a compound of Formula (I), or a metabolite thereof, or an ester of the compound of Formula (I) or the metabolite thereof, or a pharmaceutically acceptable salt of each thereof, wherein the compound of Formula (I) is defined as above.

In one embodiment, the subject is diagnosed with hyperlipoproteinemia. In another embodiment, the subject has a low density lipoprotein blood level that is considered normal.

As used herein, "a metabolite thereof" refers to a metabolite that shows substantially similar therapeutic activity as a compound of Formula (I). Non limiting examples of such metabolites include compounds where the —COCH₃ group, of a compound of Formula (I), that is attached to the phenyl containing the —O—(CH₂)ₙCO₂H moiety is metabolized to a 1-hydroxyethyl (—CH(OH)Me) group.

Metabolites containing such a 1-hydroxyethyl group contain an asymmetric center on the 1-position of the 1-hydroxyethyl group. The corresponding enantiomers and mixtures thereof, including racemic mixtures, are included within the metabolites of the compound of Formula (I) as utilized herein.

As used herein, "an ester thereof" refers to an ester of the phenolic hydroxy group and/or an ester of the carboxylic acid shown in the compound of Formula (I), and an ester of the 1-hydroxyethyl (an aliphatic hydroxy group) group of a metabolite of the compound Formula (I). An ester of the phenolic and/or the aliphatic hydroxy groups can include, without limitation, as the corresponding acid, a carboxylic acid $R_A$—CO₂H, wherein $R_A$ is $C_1$-$C_6$ alkyl, aryl, heteroaryl, $C_3$-$C_{12}$ cycloalkyl, or $C_2$-$C_8$ heterocyclyl, wherein the alkyl, aryl, heteroaryl, cycloalkyl, or heterocyclyl are optionally substituted with 1-4 $C_1$-$C_3$ alkyl, aryl, CO₂H, amino, alkylamino, or dialkylamino groups. Other acids such as mono-, di-, or tri phosphoric acids are also contemplated. An ester of the carboxylic acid can include, without limitation, as the corresponding alcohol, a compound of formula $R_A$—OH, wherein $R_A$ is defined as above. In one embodiment, only the carboxylic acid in Formula (I) is esterified. In another embodiment, only the phenolic hydroxy group in Formula (I) is esterified. In another embodiment, $R_A$ is $C_1$-$C_4$ alkyl. As will be apparent to the skilled artisan, such esters act as prodrugs that are hydrolyzed in vivo to release the compound of Formula (I) or a salt thereof.

In a preferred embodiment, the compound of Formula (I) is a compound of Formula (IA) (or MN-001):

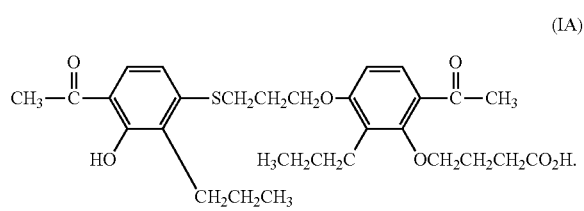

In another preferred embodiment, the metabolite of the compound of Formula (I) and (IA) is a compound of Formula (IB) (or MN-002):

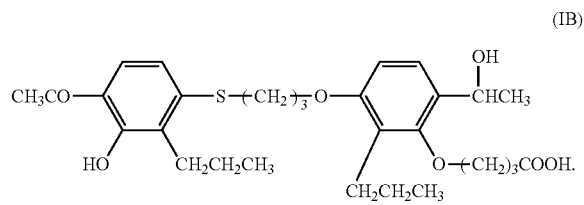

In one embodiment, the compound is administered orally. In another embodiment, the compound is administered once daily, twice daily, or thrice daily. In another embodiment, the compound is administered as a liquid or solid dosage form. In another embodiment, the compound is administered orally in a solid dosage form and is present in an orthorhombic crystalline form substantially free of other polymorphic forms. In another embodiment, the subject is considered healthy. In another embodiment, the compound is administered in an amount ranging from 50 mg/day to 5,000 mg/day, optionally divided into one, two, or three portions. In another embodiment, the compound is administered at a dosage of 25 mg, 50 mg, 75 mg, 100 mg, 150 mg, 200 mg, 250 mg, 500 mg, 750 mg, 1,000 mg 1500 mg, or 2000 mg, once a day, twice a day, or three times a day. In other embodiments, the compound is administered 50 mg qd (once daily), 50 mg bid (twice daily), 50 mg tid (thrice daily), 100 mg qd, 100 mg bid, 100 mg tid, 500 mg qd, 500 mg bid, 500 mg tid, 750 mg qd, 750 mg bid, 750 mg tid, or 500 mg tid for 5 days and then 750 mg bid for another 5 days. In other embodiments, the compound is administered, e.g., at least for 1 week, 2 weeks, 3 weeks, 4 weeks, 8 weeks, 12 weeks, or indefinitely.

Synthesis

The synthesis and certain biological activity of the compounds of Formula (I) are described in U.S. Pat. No. 4,985,585 which is incorporated herein in its entirety by reference. For example, the compound of Formula (IA) is prepared by reacting a phenol of Formula (II):

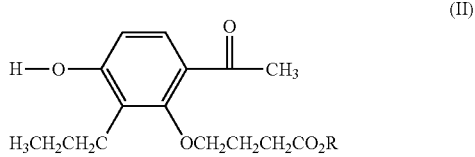

wherein, R is a carboxylic acid protecting group, with a compound of Formula (III):

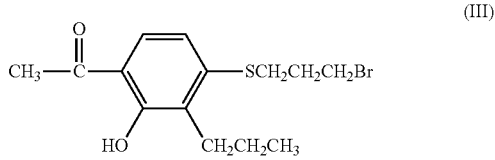

to provide a compound of Formula (IC):

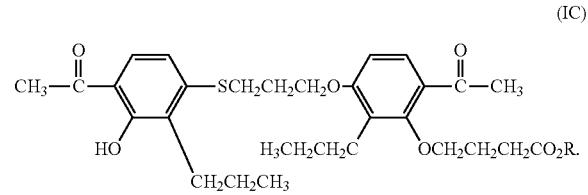

Non limiting examples of acid protecting groups, or R groups, include $C_1$-$C_6$ alkyl, benzyl, benzhydryl, and trityl, wherein the benzyl, benzhydryl, or trityl group is optionally substituted with 1-6 $C_1$-$C_6$ alkyl, halo, and/or $C_1$-$C_6$ alkoxy groups. It will be apparent to the skilled artisan that a leaving group other than the bromo group of Formula (III) may be used. Non limiting examples of such other leaving groups include chloro or tosylate.

Deprotection of the protected carboxylic acid of Formula (IC) provides the compound of Formula (IA). As is apparent based on this disclosure, compounds of Formula (IC) are in some embodiments useful in accordance with this invention. Non-limiting examples of deprotection methods include, alkaline hydrolysis and hydrogenolysis under $H_2$ and a catalyst such as Pd/C or Pt/C.

The reactions are carried out in an inert organic solvent, for example and without limitation, acetone, methylethylketone, diethylketone, or dimethylformamide. The nucleophilic displacement reaction may be conducted at a temperature below room temperature up to the reflux temperature of the solvent, in the presence of an inorganic base, such as potassium carbonate or sodium carbonate, and optionally in the presence of potassium iodide. The reactions are carried out for a period of time sufficient to provide substantial product as determined by well known methods such as thin layer chromatography and $^1$H-NMR. Other compounds utilized herein are made by following the procedures described herein and upon appropriate substitution of starting materials, and/or following methods well known to the skilled artisan. See also, U.S. Pat. No. 5,290,812 (incorporated herein in its entirety by reference).

The compound of Formula (IA) is recrystallized under controlled conditions to provide an essentially pure orthorhombic polymorph, referred to as Form A crystals (e.g., 90% or more, preferably at least 95% Form A). Polymorphic Form A and processes for producing it are described in U.S. Pat. Nos. 7,060,854 and 7,064,146; which are incorporated herein in their entirety by reference. All polymorphic forms of the compound of Formula (I) are active, but polymorphic Form A is preferred. Under certain conditions, the solubility and the bioavailability of this polymorph is superior to the other polymorphs and thus Form A may offer improved solid formulations.

Form A crystals can be obtained, For example, by dissolving the compound of Formula (IA) in 5 to 10 parts by weight of ethanol at 25-40° C. to give a yellow to orange solution. The ethanol solution is charged with 1-10 parts of water and agitated at 20-25° C. for about 15-60 minutes and then at 5-10° C. for an additional period of 1-4 hours, preferably 2.0-3.0 hours, resulting in an off-white suspension. To this suspension is added 5-15 parts of water and the mixture is agitated at 5-10° C. for an additional 1-4 hours, preferably 1.5-2.0 hours. A solid, white to off-white product is isolated by vacuum filtration and the filter cake is washed with water and dried in a vacuum at 25-40° C. for 12-24 hours.

For compounds utilized herein that exist in enantiomeric forms, such as certain metabolites of the compound of Formula (I) (for example, the compound of formula IB), the two enantiomers can be optically resolved. Such a resolution is performed, for example, and without limitation, by forming diastereomeric salt of a base such as (S)-(−)-1-(1-naphthyl) ethylamine with the corresponding carboxylic acid compound, or by separating the enantiomers using chiral column chromatography. Intermediates to such compounds, which intermediates also exist in enantiomeric forms can be similarly resolved.

Administration and Formulation

The compounds utilized herein can be administered orally, or by intravenous, intramuscular, and subcutaneous injection, or transdermal methods. Effective dosage levels can vary widely, e.g., from about 100 to 4000 mg per day. In one embodiment, the daily dosage range is 250 to 2,000 mg, given in one, two or three portions. In another embodiment, the dosage is 1000 mg twice a day. In other embodiments, suitable dosages include 1000 mg qd, 1000 mg bid, and 750 mg tid.

Actual amounts will depend on the circumstances of the patient being treated. As those skilled in the art recognize, many factors that modify the action of the active substance will be taken into account by the treating physician such as the age, body weight, sex, diet and condition of the patient, the time of administration, the rate and route of administration. Optimal dosages for a given set of conditions can be ascertained by those skilled in the art using conventional dosage determination tests.

The compounds utilized herein can be formulated in any pharmaceutically acceptable form, including liquids, powders, creams, emulsions, pills, troches, suppositories, suspensions, solutions, and the like. Therapeutic compositions containing the compounds utilized herein will ordinarily be formulated with one or more pharmaceutically acceptable ingredients in accordance with known and established practice. In general, tablets are formed utilizing a carrier such as modified starch, alone or in combination with 10% by weight of carboxymethyl cellulose (Avicel). The formulations are compressed at from 1,000 to 3,000 pounds pressure in the tablet forming process. The tablets preferably exhibit an average hardness of about 1.5 to 8.0 kp/cm$^2$, preferably 5.0 to 7.5 kp/cm$^2$. Disintegration time varies from about 30 seconds to about 15 or 20 minutes.

Formulations for oral use can be provided as hard gelatin capsules wherein the therapeutically active compounds utilized herein are mixed with an inert solid diluent such as calcium carbonate, calcium phosphate or kaolin, or as soft gelatin capsules in which the compounds are mixed with an oleaginous medium, e.g., liquid paraffin or olive oil. Suitable carriers include magnesium carbonate, magnesium stearate, talc, sugar, lactose, pectin, dextrin, starch, gelatin, tragacanth, methylcellulose, sodium carboxymethyl cellulose, a low melting wax, cocoa butter, and the like.

The compounds utilized herein can be formulated as aqueous suspensions in admixture with pharmaceutically acceptable excipients such as suspending agents, e.g., sodium carboxymethyl cellulose, methylcellulose, hydroxypropylmethyl cellulose, sodium alginate, polyvinylpyrrolidone, gum tragacanth and gum acacia; dispersing or wetting agents such as naturally occurring phosphatide, e.g., lecithin, or condensation products of an alkaline oxide with fatty acids, e.g., polyoxyethylene stearate, or condensation products of ethylene oxide with long chain aliphatic alcohols, e.g, heptadecaethylene-oxycetanol, or condensation products of ethylene oxide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monoleate. Such aqueous suspensions can also contain one or more preservatives, e.g., ethyl- or -n-propyl-p-hydroxy benzoate, one or more coloring agents, one or more flavoring agents and one or more sweetening agents, such as glycerol, sorbitol, sucrose, saccharin or sodium or calcium cyclamate.

Suitable formulations also include sustained release dosage forms, such as those described in U.S. Pat. Nos. 4,788,055; 4,816,264; 4,828,836; 4,834,965; 4,834,985; 4,996,047; 5,071,646; and, 5,133,974, the contents of which are incorporated herein in their entirety by reference.

Other forms suitable for oral administration include liquid form preparations including emulsions, syrups, elixirs, aqueous solutions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monoleate, or acacia. Aqueous solutions can be prepared by dissolving the active component in water and adding suitable colorants, flavors, stabilizing, and thickening agents. Solid form preparations may contain, in addition to the active component, colorants, flavors, stabilizers, buffers, artificial and natural sweeteners, dispersants, thickeners, solubilizing agents, and the like.

The compounds utilized herein may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example as solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds utilized herein may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds utilized herein may be formulated for administration as suppositories. In such a formulation, a low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds utilized herein may be formulated for vaginal administration. Pessaries, tampons, creams, gels, pastes, foams or sprays containing in addition to the active ingredient such carriers as are known in the art to be appropriate.

The compounds utilized herein may be formulated for nasal administration. The solutions or suspensions are applied directly to the nasal cavity by conventional means, for example, with a dropper, pipette or spray. The formulations may be provided in a single or multidose form. The patient can administer an appropriate, predetermined volume of the solution or suspension via a dropper or pipette. A spray may be administered for example by means of a metering atomizing spray pump.

The compounds utilized herein may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC), (for example, dichlorodifluoromethane, trichlorofluoromethane, or dichlorotetrafluoroethane), carbon dioxide or other suitable gases. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine. The powder carrier will form a gel in the nasal cavity. The powder composition may be presented in unit dose form for example in capsules or cartridges of, for example gelatin or blister packs from which the powder may be administered by means of an inhaler.

When desired, formulations can be prepared with enteric coatings adapted for sustained or controlled release administration of the active ingredient. A common type of controlled release formulation that may be used for the purposes of the present invention comprises an inert core, such as a sugar sphere, a first layer, coated with an inner drug-containing second layer, and an outer membrane or third layer controlling drug release from the inner layer.

The cores are preferably of a water-soluble or swellable material, and may be any such material that is conventionally used as cores or any other pharmaceutically acceptable water-soluble or water-swellable material made into beads or pellets. The cores may be spheres of materials such as sucrose/starch (Sugar Spheres NF), sucrose crystals, or extruded and dried spheres typically comprised of excipients such as microcrystalline cellulose and lactose.

The substantially water-insoluble material in the first layer is generally a "GI insoluble" or "GI partially insoluble" film forming polymer (dispersed or dissolved in a solvent). As examples may be mentioned ethyl cellulose, cellulose acetate, cellulose acetate butyrate, polymethacrylates such as ethyl acrylate/methyl methacrylate copolymer (Eudragit NE-30-D) and ammonio methacrylate copolymer types A and B (Eudragit RL30D and RS30D), and silicone elastomers. Usually, a plasticizer is used together with the polymer. Exemplary plasticizers include: dibutylsebacate, propylene glycol, triethylcitrate, tributylcitrate, castor oil, acetylated monoglycerides, acetyl triethylcitrate, acetyl butylcitrate, diethyl phthalate, dibutyl phthalate, triacetin, fractionated coconut oil (medium-chain triglycerides).

The second layer containing the active ingredient may be comprised of the active ingredient (drug) with or without a polymer as a binder. The binder, when used, is usually hydrophilic but may be water-soluble or water-insoluble. Exemplary polymers to be used in the second layer containing the active drug are hydrophilic polymers such as polyvinylpyrrolidone, polyalkylene glycol such as polyethylene glycol, gelatine, polyvinyl alcohol, starch and derivatives thereof, cellulose derivatives, such as hydroxypropylmethyl cellulose (HPMC), hydroxypropyl cellulose, carboxymethyl cellulose, methyl cellulose, ethyl cellulose, hydroxyethyl cellulose, carboxyethyl cellulose, carboxymethyl hydroxyethyl cellulose, acrylic acid polymers, polymethacrylates, or any other pharmaceutically acceptable polymer. The ratio of drug to hydrophilic polymer in the second layer is usually in the range of from 1:100 to 100:1 (w/w).

Suitable polymers for use in the third layer, or membrane, for controlling the drug release may be selected from water insoluble polymers or polymers with pH-dependent solubility, such as, for example, ethyl cellulose, hydroxypropylmethyl cellulose phthalate, cellulose acetate phthalate, cellulose acetate trimellitate, polymethacrylates, or mixtures thereof, optionally combined with plasticizers, such as those mentioned above.

Optionally, the controlled release layer comprises, in addition to the polymers above, another substance(s) with different solubility characteristics, to adjust the permeability, and thereby the release rate, of the controlled release layer. Exemplary polymers that may be used as a modifier together with, for example, ethyl cellulose include: HPMC, hydroxyethyl cellulose, hydroxypropyl cellulose, methylcellulose, carboxymethylcellulose, polyethylene glycol, polyvinylpyrrolidone (PVP), polyvinyl alcohol, polymers with pH-dependent solubility, such as cellulose acetate phthalate or ammonio methacrylate copolymer and methacrylic acid copolymer, or mixtures thereof. Additives such as sucrose, lactose and pharmaceutical grade surfactants may also be included in the controlled release layer, if desired.

Also provided herein are unit dosage forms of the formulations. In such forms, the formulation is subdivided into unit dosages containing appropriate quantities of the active component (e.g., and without limitation, a compound of Formula (I) or an ester thereof, or a salt of each thereof). The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa.

EXAMPLES

Example 1

Reduction of Triglyceride Levels in Human Subjects Upon MN-001 Administration

Human subjects were administered various daily amounts of MN-001 and placebo and their triglyceride blood levels (mg/deciliter or dl) measured at various time points. As tabulated below, administration of MN-001 demonstrated, with certain exceptions, a substantial lowering of mean triglyceride blood levels compared to control subjects (placebo) in accordance with the present invention. As to the "week 14" time point in Table 1-D, it provides triglyceride levels of follow-up patients after MN-001 administration was stopped at 12 weeks. Yet, as the data demonstrate for the treatment groups, triglyceride levels continued their downward trend during this follow-up period compared with a control group.

TABLE 1-A (Asthma Subjects)

| Time point | Placebo (N = 36) | 500 mg tid (N = 36) | 750 mg bid (N = 36) | 750 mg qd (N = 36) |
|---|---|---|---|---|
| Screening | 132.3 | 109.5 | 125.5 | 112.2 |
| Week 4 | 126.9 | 91.6 | 98.5 | 117.2 |

TABLE 1-B (Interstitial Cystitis Subjects)

| Time point | Placebo (N = 100) | 500 mg qd (N = 94) | 500 mg bid (N = 106) |
|---|---|---|---|
| Baseline | 144.3 | 136.1 | 135.7 |
| Week 4 | 144.5 | 109.5 | 106.7 |
| Week 8 | 138.8 | 124.7 | 110.7 |

TABLE 1-C (Healthy Subjects)

| Time point | 1500 mg/day × 10 days (N = 11)[#] |
|---|---|
| Screening | 145.4 |
| Day 11 | 87.5 |

[#] Dose/Duration = 500 mg TID × 5 days then 750 mg BID × 5 days OR 750 mg BID × 5 days then 500 mg TID; Total 10 days

TABLE 1-D (Asthma Subjects)

| Time point | Placebo (N = 44) | 500 mg tid (N = 54) | 750 mg bid (N = 53) |
|---|---|---|---|
| Baseline | 135.4 | 159.4 | 117.0 |
| Week 4 | 123.1 | 112.5 | 94.1 |
| Week 8 | 167.6 | 132.4 | 101.4 |
| Week 12 | 142.6 | 147.7 | 114.0 |
| Week 14 | 155.2 | 134.1 | 104.6 |

Example 2

Reduction of Total Cholesterol Levels in Human Subjects Upon MN-001 Administration Human subjects were administered various daily amounts of MN-001 and placebo and their total cholesterol blood levels (mg/dl) measured at various time points. As tabulated below, administration of MN-001 demonstrated, with certain exceptions, a substantial lowering of mean total cholesterol blood levels compared to control subjects (placebo) in accordance with the present invention.

TABLE 2-A (Asthma Subjects)

| Time point | Placebo (N = 36) | 500 mg tid (N = 36) | 750 mg bid (N = 36) | 750 mg qd (N = 36) |
|---|---|---|---|---|
| Screening | 197.5 | 193.5 | 180.5 | 191.5 |
| Week 4 | 199.7 | 183.1 | 181.6 | 180.6 |

TABLE 2-B (Interstitial Cystitis Subjects)

| Time point | Placebo (N = 100) | 500 mg qd (N = 94) | 500 mg bid (N = 106) |
|---|---|---|---|
| Baseline | 169.4 | 173.8 | 174.5 |
| Week 4 | 167.8 | 171.5 | 169.8 |
| Week 8 | 166.7 | 170.5 | 168.7 |

TABLE 2-C (Healthy Subjects)

| Time point | 1500 mg/day × 10 days (N = 11)* |
|---|---|
| Screening | 176.9 |
| Day 11 | 167.8 |

*For dose amount and frequency of administration, see Table 1-C.

TABLE 2-D (Asthma Subjects)

| Time point | Placebo (N = 44) | 500 mg tid (N = 54) | 750 mg bid (N = 53) |
|---|---|---|---|
| Baseline | 198.1 | 182.5 | 185.4 |
| Week 4 | 192.0 | 179.3 | 181.6 |

TABLE 2-D-continued (Asthma Subjects)

| Time point | Placebo (N = 44) | 500 mg tid (N = 54) | 750 mg bid (N = 53) |
|---|---|---|---|
| Week 8 | 194.3 | 176.9 | 187.3 |
| Week 12 | 221.4 | 169.6 | 192.4 |
| Week 14* | 200.1 | 182.8 | 182.6 |

*As to the "week 14" time point, it relates to follow-up patients after MN-001 administration was stopped at 12 weeks.

Example 3

Reduction of Low Density Lipoprotein (LDL) in Human Subjects Upon MN-001 Administration Human subjects were administered various daily amounts of MN-001 and placebo and their total LDL blood levels (mg/dl) measured at various time points. As tabulated in Tables 3A-D, administration of MN-001 demonstrated, with certain exceptions, a substantial lowering of mean LDL blood levels compared to control subjects (placebo) in accordance with the present invention. Advantageously, blood levels of HDL, which plays a positive role in cholesterol transport and metabolism, are not altered substantially, if at all, upon administration of MN-001.

TABLE 3-A (Asthma Subjects)

| Time point | Placebo (N = 36) | 500 mg tid (N = 36) | 750 mg bid (N = 36) | 750 mg qd (N = 36) |
|---|---|---|---|---|
| Screening | 113.9 | 113.8 | 100.3 | 115.7 |
| Week 4 | 117.1 | 105.4 | 104.7 | 106.9 |

TABLE 3-B (Interstitial Cystitis Subjects)

| Time point | Placebo (N = 100) | 500 mg qd (N = 94) | 500 mg bid (N = 106) |
|---|---|---|---|
| Baseline | 55.6 | 65.8 | 62.6 |
| Week 4 | 50.9 | 60.1 | 54.5 |
| Week 8 | 50.1 | 55.5 | 52.2 |

TABLE 3-C (Healthy Subjects)

| Time point | 1500 mg/day × 10 days (N = 11)* |
|---|---|
| Screening | 99.1 |
| Day 11 | 103.0 |

*For dose amount and frequency of administration, see Table 1-C.

TABLE 3-D (Asthma Subjects)

| Time point | Placebo (N = 44) | 500 mg tid (N = 54) | 750 mg bid (N = 53) |
|---|---|---|---|
| Baseline | 112.9 | 100.2 | 106.3 |
| Week 4 | 109.2 | 99.5 | 102.3 |
| Week 8 | 110.6 | 99.1 | 106.6 |
| Week 12 | 142.6 | 92.5 | 110.9 |
| Week 14* | 109.9 | 102.6 | 103.6 |

*As to the "week 14" time point, it relates to follow-up patients after MN-001 administration was stopped at 12 weeks.

What is claimed is:

1. A method of reducing a triglyceride blood level in a subject, consisting essentially of administering to a subject in need thereof an effective amount of a compound of Formula (I):

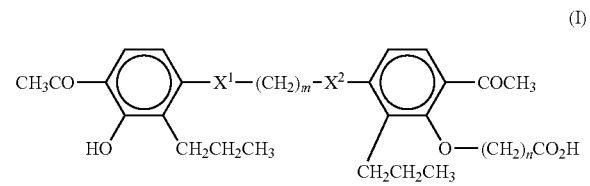

an ester of the compound of Formula (I), or a pharmaceutically acceptable salt of each of the foregoing, in which m is an integer from 2 to 5, n is an integer from 3 to 8, $X^1$ and $X^2$ each independently represent a sulfur atom, oxygen atom, sulfinyl group, or a sulfonyl group, provided that $X^1$ and $X^2$ cannot both be oxygen atoms, wherein the effective amount is about 50 mg to about 5000 mg per day.

2. The method of claim 1, in which the compound of Formula (I) is of Formula (IA)

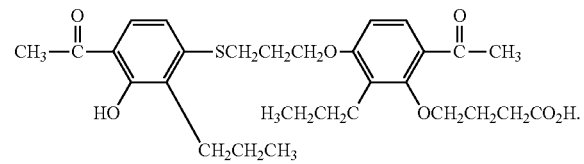

3. The method of claim 1, in which the compound of Formula (I) is a compound of Formula (IB):

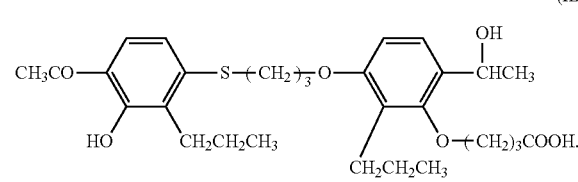

4. The method of claim 1, in which the subject is diagnosed with hypertriglyceridemia.

5. The method of claim 1, in which the compound is administered orally.

6. The method of claim 1, in which the compound is administered once daily, twice daily, or thrice daily.

7. The method of claim 1, in which the compound is administered as a liquid or solid dosage form.

8. The method of claim 2, in which the compound is administered orally in a solid dosage form and is present in an orthorhombic crystalline form.

9. The method of claim 1, in which the compound is administered at a dosage of 50 mg, 75 mg, 100 mg, 200 mg, 500 mg, 750 mg, or 1,000 mg once a day, twice a day, or three times a day.

10. A method of reducing a total cholesterol blood level in a subject, comprising administering to a subject in need thereof an effective amount of a compound of Formula (I):

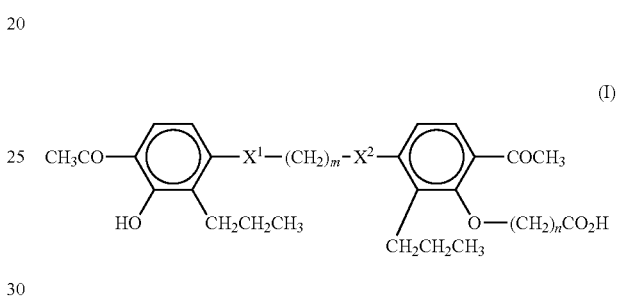

an ester of the compound of Formula (I), or a pharmaceutically acceptable salt of each of the foregoing, in which m is an integer from 2 to 5, n is an integer from 3 to 8, $X^1$ and $X^2$ each independently represent a sulfur atom, oxygen atom, sulfinyl group, or a sulfonyl group, provided that $X^1$ and $X^2$ cannot both be oxygen atoms.

11. The method of claim 10, in which the compound of Formula (I) is of Formula (IA):

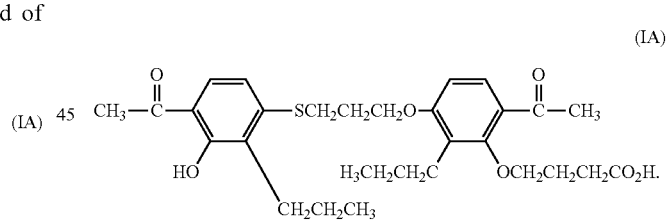

12. The method of claim 10, in which the compound of Formula (I) is a compound of Formula (IB):

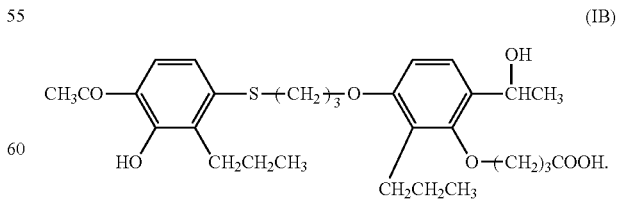

13. The method of claim 10, in which the subject is diagnosed with hypercholesterolemia.

14. The method of claim 10, in which the compound is administered orally.

15. The method of claim 10, in which the compound is administered once daily, twice daily, or thrice daily.

16. The method of claim 10, in which the compound is administered as a liquid or solid dosage form.

17. The method of claim 11, in which the compound is administered orally in a solid dosage form and is present in an orthorhombic crystalline form.

18. The method of claim 10, in which the compound is administered in an amount ranging from 50 mg/day to 5,000 mg/day, optionally divided into one, two, or three portions.

19. The method of claim 10, in which the compound is administered at a dosage of 50 mg, 75 mg, 100 mg, 200 mg, 500 mg, 750 mg, or 1,000 mg once a day, twice a day, or three times a day.

20. A method of reducing a low density lipoprotein (LDL) blood level in a subject, comprising administering to a subject in need thereof an effective amount of a compound of Formula (I):

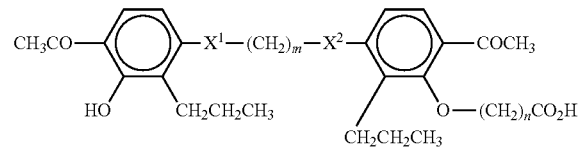

(I)

an ester of the compound of Formula (I), or a pharmaceutically acceptable salt of each of the foregoing, in which m is an integer from 2 to 5, n is an integer from 3 to 8, $X^1$ and $X^2$ each independently represent a sulfur atom, oxygen atom, sulfinyl group, or a sulfonyl group, provided that $X^1$ and $X^2$ cannot both be oxygen atoms.

21. The method of claim 20, in which the compound of Formula (I) is of Formula (IA)

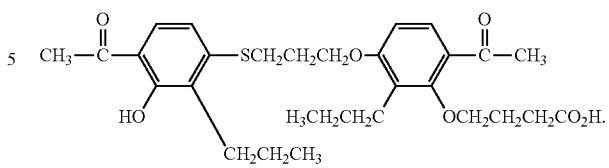

(IA)

22. The method of claim 20, in which the compound of Formula (I) is a compound of Formula (IB):

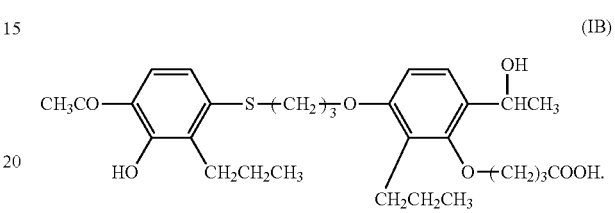

(IB)

23. The method of claim 20, in which the subject is diagnosed with hyperlipoproteinemia.

24. The method of claim 20, in which the compound is administered orally.

25. The method of claim 20, in which the compound is administered once daily, twice daily, or thrice daily.

26. The method of claim 20, in which the compound is administered as a liquid or solid dosage form.

27. The method of claim 21, in which the compound is administered orally in a solid dosage form and is present in an orthorhombic crystalline form.

28. The method of claim 1, in which the subject has a triglyceride blood level that is considered normal.

29. The method of claim 1, in which the subject is considered healthy.

* * * * *